(12) United States Patent
Medoff

(10) Patent No.: US 8,906,070 B2
(45) Date of Patent: Dec. 9, 2014

(54) BONE FIXATION DEVICE AND METHOD

(75) Inventor: Robert J. Medoff, Kailua, HI (US)

(73) Assignees: Robert J. Medoff, Kailua, HI (US);
Lars G. Tellman, Falsterbo (SE); David Medoff, Valencia, CA (US)

( * ) Notice: Subject to any disclaimer, the term of this patent is extended or adjusted under 35 U.S.C. 154(b) by 1172 days.

(21) Appl. No.: 11/257,854

(22) Filed: Oct. 25, 2005

(65) Prior Publication Data

US 2007/0123880 A1    May 31, 2007

(51) Int. Cl.
*A61B 17/80* (2006.01)

(52) U.S. Cl.
CPC ......... *A61B 17/8007* (2013.01); *A61B 17/8061* (2013.01); *A61B 17/8085* (2013.01); *A61B 17/809* (2013.01)
USPC ....................................................... 606/280

(58) Field of Classification Search
USPC ........... 606/280, 283–285, 60, 101, 151, 282, 606/297, 902–904, 291, 906
See application file for complete search history.

(56) References Cited

U.S. PATENT DOCUMENTS

| | | | |
|---|---|---|---|
| 4,269,180 A * | 5/1981 | Dall et al. | 606/281 |
| 4,565,193 A * | 1/1986 | Streli | 606/297 |
| 4,651,724 A * | 3/1987 | Berentey et al. | 606/284 |
| 4,969,886 A * | 11/1990 | Cziffer et al. | 606/59 |
| 5,197,966 A * | 3/1993 | Sommerkamp | 606/286 |
| 5,718,704 A * | 2/1998 | Medoff | 606/286 |
| 5,718,705 A * | 2/1998 | Sammarco | 606/284 |
| 5,931,839 A * | 8/1999 | Medoff | 606/286 |
| 6,123,709 A * | 9/2000 | Jones | 606/281 |
| 6,235,032 B1 * | 5/2001 | Link | 606/280 |
| 6,283,969 B1 * | 9/2001 | Grusin et al. | 606/280 |
| 6,338,734 B1 * | 1/2002 | Burke et al. | 606/281 |
| 7,229,444 B2 * | 6/2007 | Boyd | 606/300 |
| 2002/0058940 A1 * | 5/2002 | Frigg et al. | 606/69 |
| 2003/0040748 A1 * | 2/2003 | Aikins et al. | 606/70 |
| 2004/0102775 A1 * | 5/2004 | Huebner | 606/69 |
| 2004/0111089 A1 * | 6/2004 | Stevens et al. | 606/69 |
| 2004/0116930 A1 * | 6/2004 | O'Driscoll et al. | 606/69 |
| 2004/0210220 A1 * | 10/2004 | Tornier | 606/69 |
| 2005/0015089 A1 * | 1/2005 | Young et al. | 606/69 |
| 2005/0085818 A1 * | 4/2005 | Huebner | 606/69 |
| 2006/0200145 A1 * | 9/2006 | Kay et al. | 606/69 |
| 2006/0264949 A1 * | 11/2006 | Kohut et al. | 606/69 |
| 2008/0119895 A1 * | 5/2008 | Manceau | 606/280 |

FOREIGN PATENT DOCUMENTS

WO          WO 9809578 A1 *   3/1998

* cited by examiner

*Primary Examiner* — Christian Sevilla
(74) *Attorney, Agent, or Firm* — Ladas & Parry LLP

(57) ABSTRACT

For fixation of an oblique fracture in a long bone, a fixation plate is placed along the bone across the fracture and tabs extending outwardly from the plate engage the bone at upper and lower surfaces respectively of the proximal and distal fragments of the bone. By applying compressive force to the bone by the tabs, the fragments are subjected to compression force across the fracture and to a torque which opposes bone shortening.

25 Claims, 7 Drawing Sheets

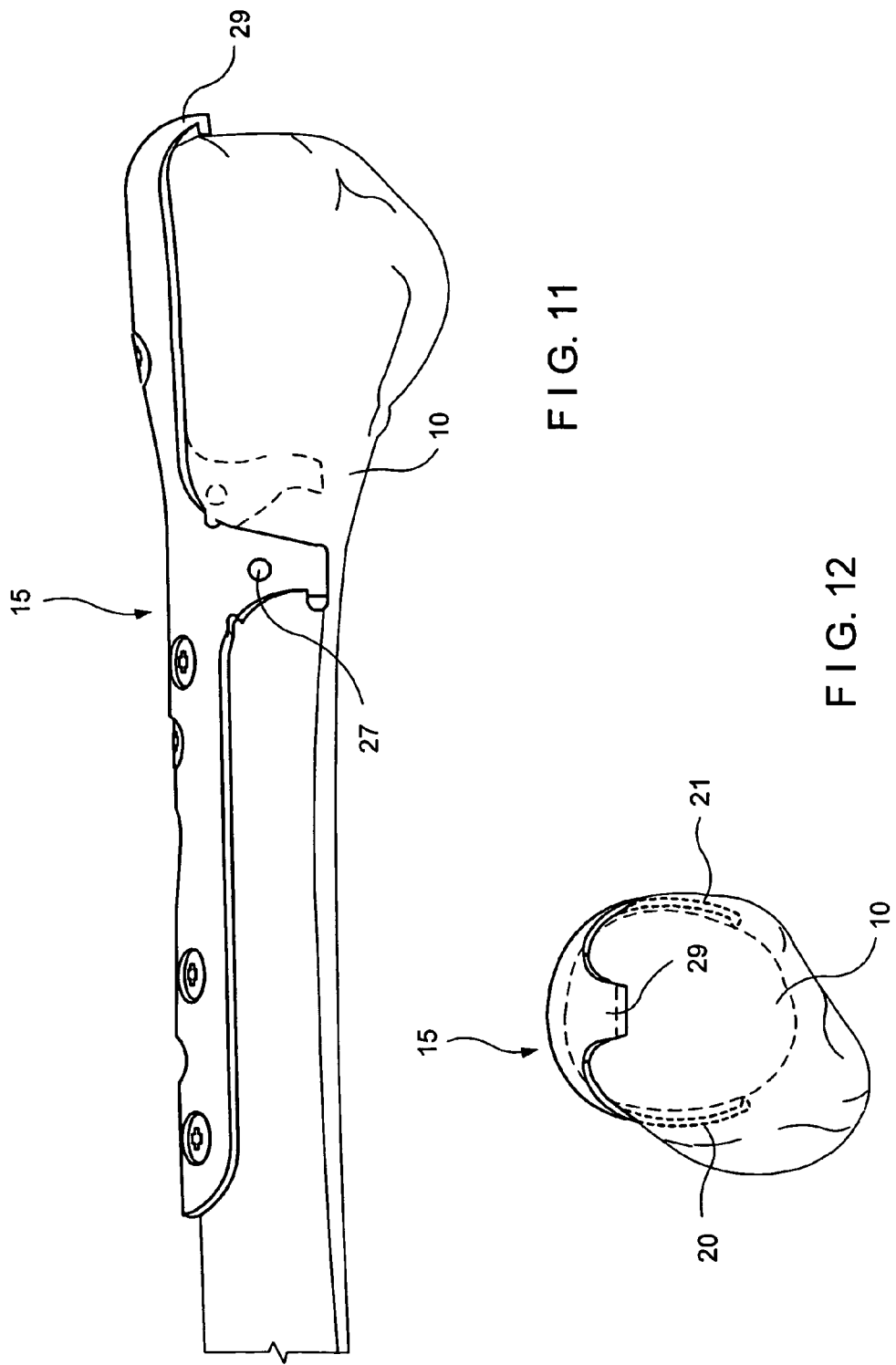

BONE FIXATION DEVICE AND METHOD

FIELD OF THE INVENTION

The invention relates to a bone fixation device used for fixation of two bone fragments or segments that have an oblique surface of contact, such as the case with an oblique fracture of the lateral malleolus of the ankle.

The invention further relates to a method of bone fixation of such oblique fractures.

BACKGROUND AND PRIOR ART

Achieving stable fixation of two bone segments having an oblique contact surface can be difficult. For example, external rotation injuries of the ankle may often result in a short oblique fracture of the lateral malleolus. Because of the oblique orientation of the fracture line, simple apposition of the bone surfaces is nearly always unstable, since axial loading forces on the bone cause sliding of the two bone surfaces along the oblique fracture line and contribute to potential problems of shortening, non-union, and loss of reduction. For fractures involving the lateral malleolus of the ankle, even as little as 1 millimeter of shortening can lead to debilitating arthritis and ankle instability.

In the case of an oblique fracture of the lateral malleolus, the opposing bone ends of segments or fragments have the tendency to slide in opposite directions and shorten since axial loading of the bone produces shear stresses contributed by the obliquity of the fracture surface. This will be explained with reference to FIG. 1. If a reference point C is considered at the exact center of the fracture, axial forces F on the bone segments 1,2 produce sliding of the segments along the oblique fracture in opposite directions. The displacement of the two bone segments 1,2 in opposite directions causes the axial forces F on either side of the fracture to displace off center, resulting in the production of a force couple or torque T that aggravates the instability. This torque across the fracture site leads to additional displacement of the bone segments 1,2 and shortening of the bone.

A conventional arrangement of treating oblique fractures of the lateral malleolus of the ankle is illustrated in FIG. 2 which comprises inserting two interfragmentary screws or pins 5 across the fracture site. The interfragmentary screws 5 produce simple side to side compression of the oblique fracture surfaces. Because the fracture is oblique and the screws 5 only have a single point of fixation 6 on each side of the fracture surface of fracture 3, the screws 5 rely only on frictional forces across the fracture site to prevent sliding of the oblique surfaces and resultant shortening. Often such interfragmentary screws 5 cannot be placed perpendicular to the plane of the fracture, which results in a contribution of a force component that adds shear to the fracture site. This is similar to the way a wedge will tend to slip out of a vise as the vise is tightened.

Furthermore, since interfragmentary fixation relies on a single point of contact of the screw within each bone fragment 1,2, there is poor resistance to angular displacements and loss of reduction with axial loading of the bone as shown in FIG. 3.

Even if the screws 5 can be placed perpendicular to the fracture, this manner of fixation is not optimal since the bone is often osteoporotic with the result that the threads of the screws strip and lose purchase as compression is applied.

In addition, placing relatively large diameter holes in a small bone fragment can result in further fracture propagation through the screw hole. These factors limit the amount of compression that can be achieved by simple interfragmentary bone screw 5.

Fixation with interfragmentary screws is based entirely on the use of one or two screws. The holding power of the screws is based entirely on the purchase of the screw threads in the thin cortex of the bone fragments 1,2, which is often tenuous. In addition, this type of fixation is extremely weak in resisting external rotational torque T on the ankle, which can also lead to failure of fixation and a poor clinical result.

Another traditional means for fixation of oblique fractures is shown in FIG. 4 in which a bone plate 7 is utilized. Such a bone plate is used to statically hold the fragments 1, 2 in position without any compression (so called neutralization plates) or to hold the bone and create compression along the long axis of the bone (so called compression plates). Neutralization plates do not produce compression at the fracture site but instead depend entirely on the purchase of bone screw 8 on either side of the fracture and the strength of the plate. Fixation is along a single axis and in one plane and is relatively weak in resisting torsional loads. In addition, this type of fixation requires bulky plates and a multitude of screws with larger surgical incisions. Neutralization plates do not provide any load across the fracture site, and may result in longer healing times as well.

Compression plates which produce compression along the axis of the bone are effective for stable fixation of simple fractures that are transverse (not oblique) to the long axis of the bone. However, using a compression plate in the context of a long oblique fracture produces shear forces at the fracture site as previously described, resulting in sliding of the bone fragments with shortening and loss of reduction. In addition, since the plate is situated predominantly within a single plane, like neutralization plates, they provide only a single plane of fixation with limited ability to control rotational forces.

Recently, a plate for distal radius fractures has been used in which there is a small tab extending from a distal edge of the plate to act as a gutter to catch an edge of the bone. However, this tab is designed as a positional reference for the plate to the edge of the bone and is positioned at the extreme distal edge of the plate. Because it does not extend deeply, rotation of the plate would not produce any translational force to the bone, but rather would cause the bone to slip out from under the tab. In addition, the extreme distal nature of the position of this tab would cause the distal fragment to rotate off the corner of the plate.

Another technique for fixation of long bone fractures is the use of intramedullary pinning or rodding. Intramedullary fixation is not effective for short oblique fractures as it provides no rotational control and allows shortening of the bone.

SUMMARY OF THE INVENTION

An object of the invention is to provide a method and apparatus for fixation of a fracture using an implant that produces compressive load (oblique or perpendicular) to the long axis of the implant across an oblique fracture line in order to facilitate healing and avoid further shortening of the two bone fragments.

A further object of the invention is to provide such fixation in which a counter-rotational torque is generated to prevent sliding of the fragments and production of a destabilizing force couple.

A further object of the invention is to provide a device that is simple to apply, reduces the risk of iatrogenic comminution from screw holes near the fracture site, allows improved resistance to rotational torque, and avoids shortening at the fracture site.

A further object of the invention is to provide a device that provides multiple planes of fixation and is effective in resisting shortening, shearing, and rotation at the fracture site.

In accordance with the invention, a fracture fixation device is provided which comprises a fixation plate, having tabs that extend out of the plane of the plate on opposite edges; the tabs extend a sufficient distance and are sufficiently rigid such that the tabs contact the bone above and below the fracture line to apply compressive forces to the bone in a transverse direction (i.e. oblique or perpendicular to the long axis of the plate) in order to develop compression of the bone fragment along the fracture line.

In a further accordance with the invention, the tabs are situated such that rotation of the plate causes the tabs to apply compression forces on the bone fragments on either side of the fracture while at the same time limiting shortening of the bone across the fracture site, effectively producing a counter rotational torque the oblique fracture site and multiple plane fixation of the bone fragments.

According to a feature of the invention, an instrument such as a bending tool is used to enable the surgeon to further bend the tabs against the bone both to customize the degree of contact as well as to augment compression at the fracture site. In this way, the tabs serve as a means for controlling the intensity of the compressive force at the fracture site.

According to a further feature of the invention, the tabs are shaped with stress relief notches or holes to direct bending of the tab to a particular location.

According to a further feature of the invention, the tabs are configured to have projections to dig into the surface of the bone and improve fixation of the bone by the tabs.

In another feature of the invention, the tabs are provided with holes or key-ways to allow the bending tool to lock into the plate during bending of the tabs.

According to another feature of the invention, the tabs are longitudinally offset to provide contact with the opposite bone surfaces in an offset position, in order to compensate for an oblique fracture as well as to increase the lever arm for increased counter-rotational torque.

According to another feature of the invention, the tabs extend a sufficient distance away from the edge of the plate to prevent the engaged fragment from rotating off the edge of the plate as compression is applied.

According to another feature of the invention, the tabs allow placement of a screw, peg or wire to augment fixation by the tabs along an axis that is out of the plane of the plate; in one embodiment, this fixation element is threaded into the tab to lock it therein; in another embodiment, a single screw, peg, wire or bolt is passed from one tab oblique to the other and secured by threading in the tab, locking it with a nut, or crimping it into the tab.

According to another feature of the invention, one or more of the bone screw holes in the plate is oblong, to allow sliding of the plate along the bone on a partially inserted screw in order to fine tune the position of the bone fragments before fixation; in one embodiment, this oblong hole is oriented oblique to the longitudinal axis of the plate, so that as the plate is slid along the partially inserted screw, the oblique orientation of the hole causes the plate to rotate, with the result that the tab is compressed against the surface of the bone.

According to another feature of the invention, the plate is curved along its long axis to conform with the curvature of the bone, with or without a second curvature across the width of the plate, in order to allow more intimate apposition to the bone, e.g. the lateral malleolus of the ankle.

The invention also provides a method of fixation of an oblique fracture of a bone, such as the lateral malleolus of an ankle, which comprises the steps of:

reducing the fracture by abutting proximal and distal fragments along the oblique fracture applying a fixation plate along the fractured bone and across the fracture such that a first portion of the fixation plate is adjacent to the distal fragment and a second portion of the fixation plate is adjacent to the proximal fragment, providing tabs extending from the first and second portions of the fixation plate at locations spaced longitudinally of the plate and at positions at which one tab faces an upper surface of the bone while another tab faces a lower surface of the bone, and bringing the tabs into contact with the upper and lower surfaces of the bone to apply force to the distal and proximal fragments of the bone and produce compression of the distal and proximal fragments across the fracture.

Instead of providing tabs at the first and second portions of the fixation plate, a tab can be provided at only one portion of the fixation plate. In such case, the tab is sufficiently long and rigid to engage and apply transverse force to the bone such that after the other portion of the fixation plate is secured to the other bone fragment by bone screws, the tab can be brought into contact with the surface of the bone to produce the transverse force on the bone and the compression of the bone fragments along the oblique fracture line.

BRIEF DESCRIPTION OF THE FIGURES OF THE DRAWING

FIG. 11 is a side view of FIG. 10.

FIG. 12 is an end view from the right end of FIG. 10.

DETAILED DESCRIPTION

Figure 1:
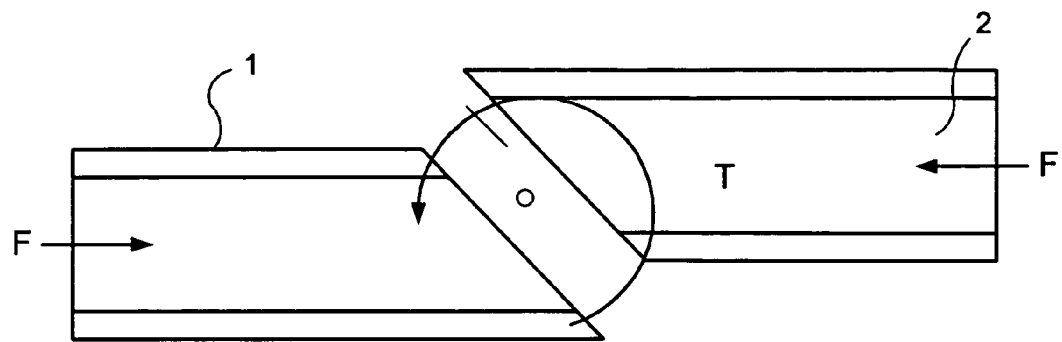
FIG. 1 is a side view illustrating a conventional oblique fracture of a bone in which the bone fragments have been displaced.
Figure 2:
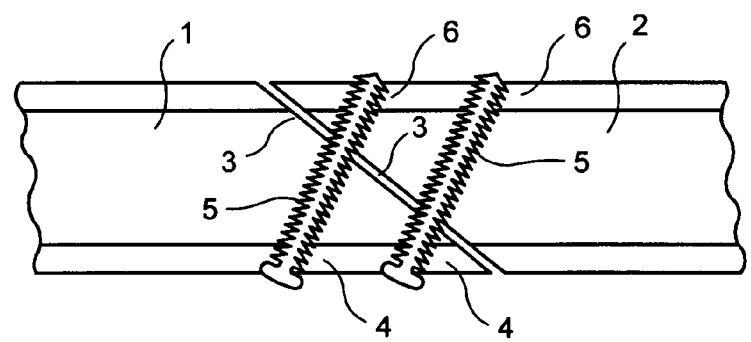
FIG. 2 illustrates a conventional arrangement for fixation of an oblique fracture.
Figure 3:
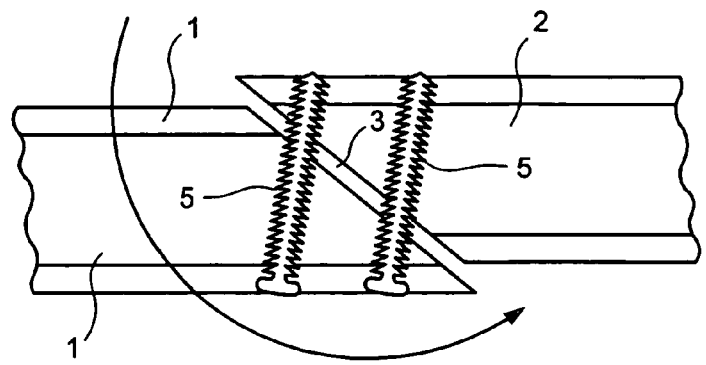
FIG. 3 shows the arrangement of FIG. 2 in which the fragments are displaced by application of a torque at the fracture.
Figure 4:
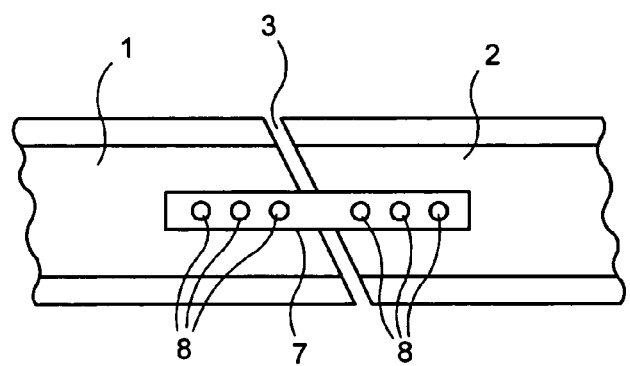
FIG. 4 illustrates another conventional arrangement for fixation of the fracture.
Figure 5:
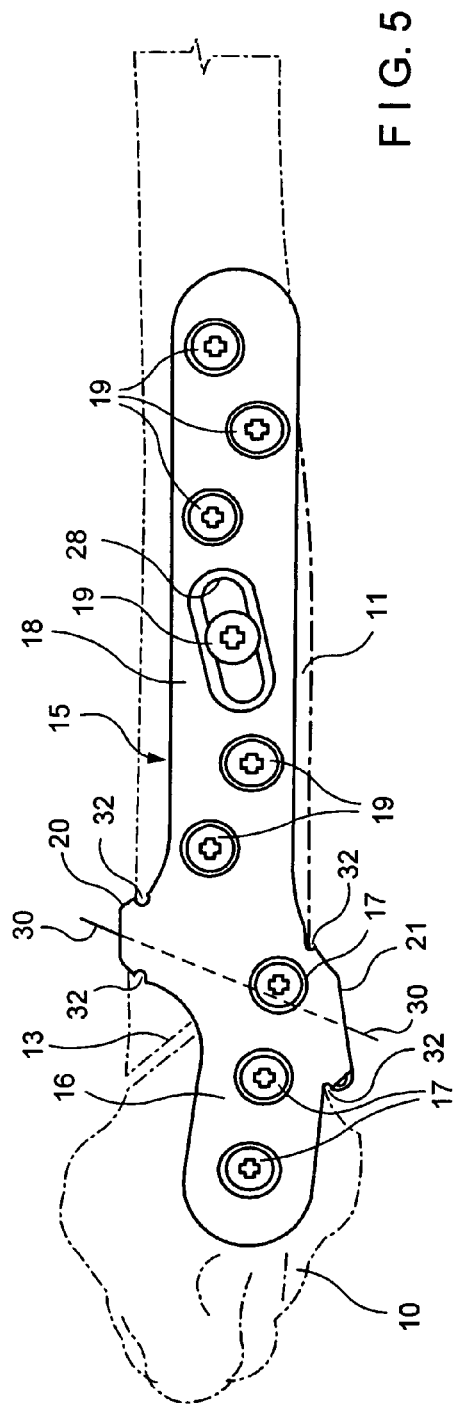
FIG. 5 is a side elevational view of the fixation device according to the invention installed on a bone having an oblique fracture.
Figure 6:
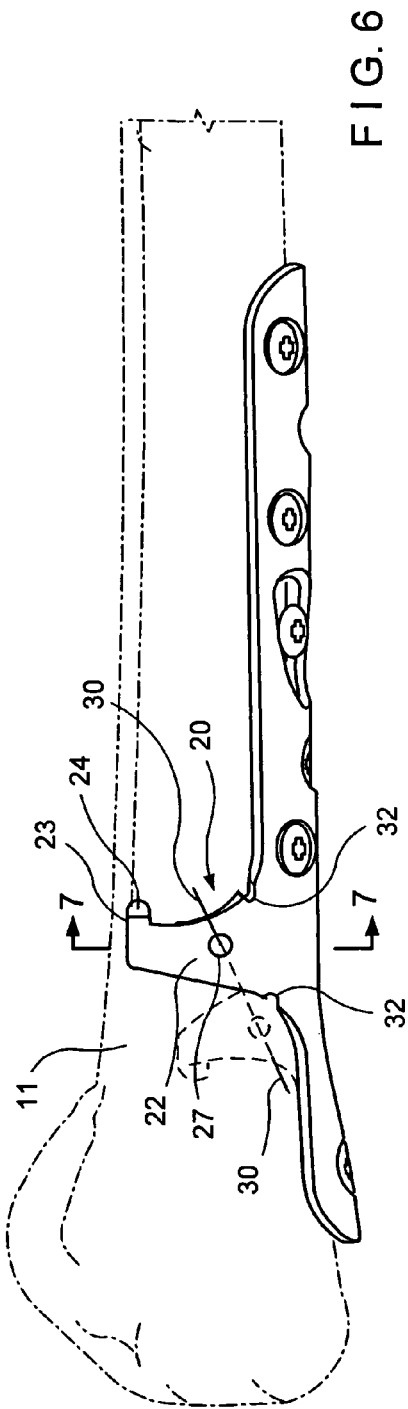
FIG. 6 is a top view of FIG. 5.

Referring to FIGS. 5 and 6, therein is shown distal and proximal bone segments or fragments 10, 11 on opposite sides of an oblique fracture 13 of the lateral malleolus bone 14 of the ankle. Although the invention will be described with reference to the lateral malleolus, it is applicable to oblique fractures of other long bones such as the ulna, humerus, tibia, femur etc.

Attached to the side of the bone 14 is a fixation plate 15 of a fixation implant for fixation of the fracture 13. The fixation plate 15 has a distal portion 16 adapted for being secured by bone screws 17 to the distal fragment 10 and a proximal portion 18 adapted to be secured to the proximal fragment 11 by bone screws 19.

The fixation plate 15 is made of surgical material such as titanium or stainless steel. Its length and thickness is a function of the bone which is fractured. In a typical case of the lateral malleolus, the thickness of plate 15 will be between 0.025" and 0.375" and its length will be between 0.5" and 5.0". For fractures of other bones, the dimensions of the fixation plate will be determined by the surgeon as is well known in the art. The fixation plate is required to have sufficient rigidity to secure the fragments in a stable position.

Figure 9:
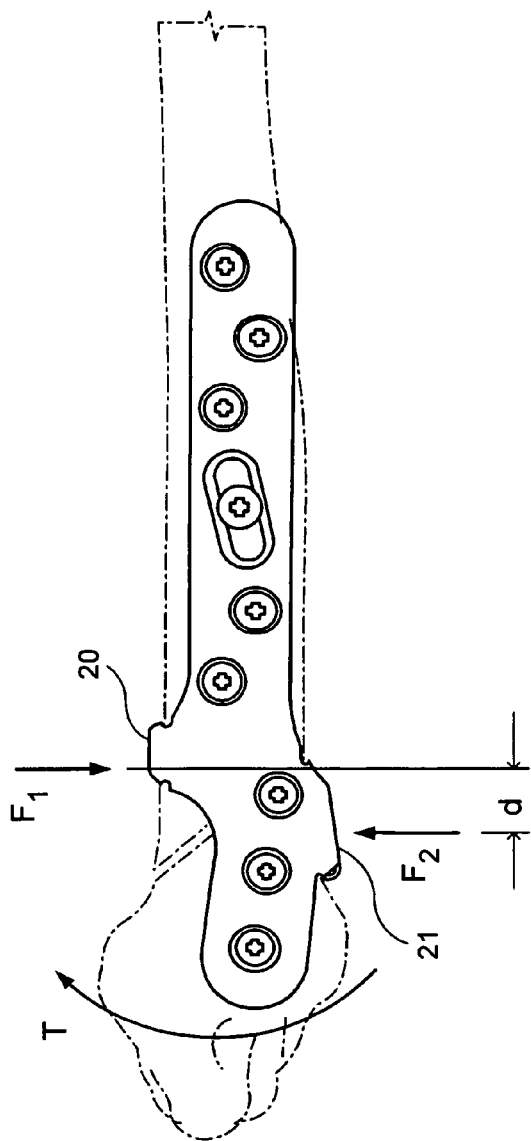
FIG. 9 is an explanatory view showing the forces acting on the bone with reference to the fixation device of FIG. 6.

At the upper edge of proximal portion 18, a tab 20 extends outwards of the fixation plate 15 and at the lower edge of the distal portion 16, a tab 21 extends outwards of the fixation plate 15 in the opposite direction of tab 20. The tabs 20 and 21 are longitudinally spaced from one another (by a distance d as shown in FIG. 9) and are disposed on opposite sides of the fracture 13 such that tab 20 is disposed above the fracture 13 whereas tab 21 is disposed below the fracture 13.

Figure 13:
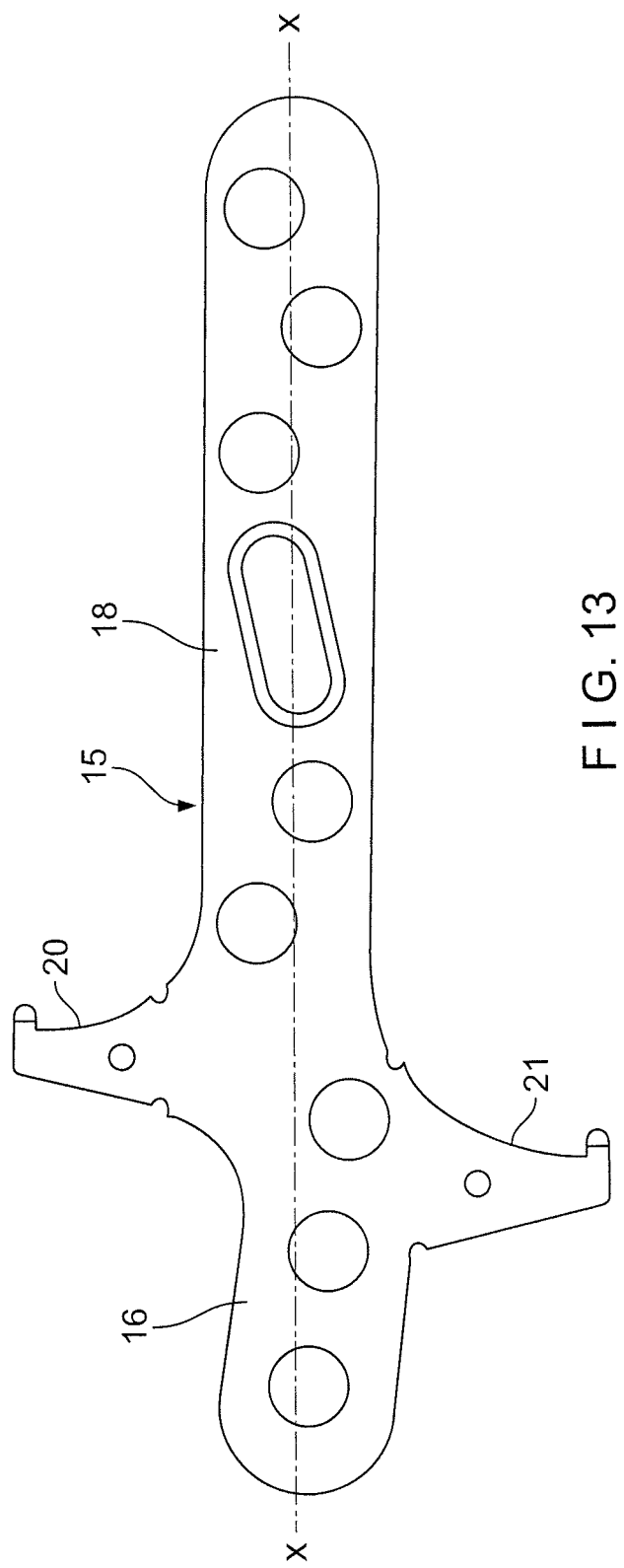
FIG. 13 is a side elevational view of the fixation plate with tabs thereof upfolded in the plane of the plate.

As seen in FIGS. 5,6 and 13 it is seen that tabs 20 and 21 extend outwardly from the proximal and distal fragments along lines which intersect longitudinal axis X-X of plate 15 at points of intersection which are spaced from one another along the longitudinal axis to produce a torque T (as will be described in more detail later) opposing destabilization of the fracture.

Figure 8:
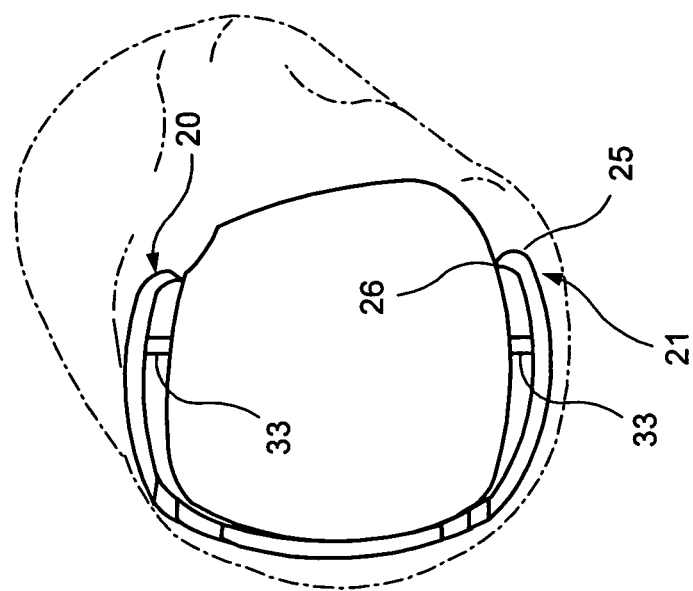
FIG. 8. is an end view seen from the right end of FIG. 5.
Figure 7:
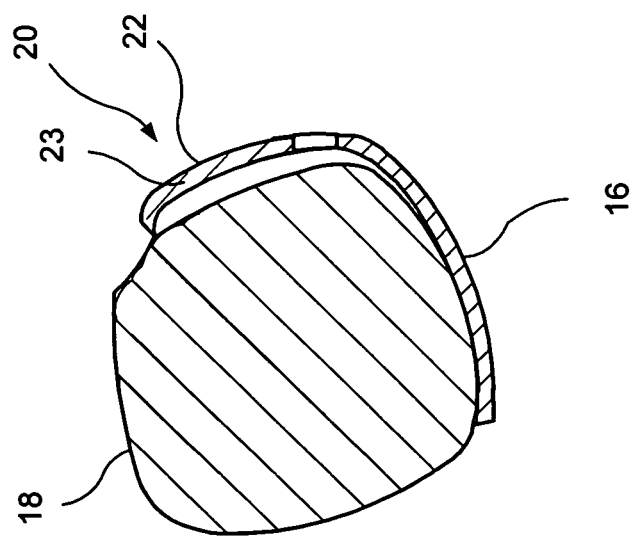
FIG. 7 is a sectional view taken on line 7-7 in FIG. 6.

As seen in FIGS. 7 and 8, tab 20 has an extending leg portion 22 which extends around the upper surface of the proximal fragment 11. The leg portion 22 has a lower end 23 with a pointed tip 24 forming a tooth.

Tab 21 is a mirror image of tab 20 and has the same shape as tab 20 and includes leg portion 25 and pointed tip 26.

The tabs 20 and 21 are intended to be bent against the respective bone fragments. The teeth of pointed tips 24 and 26 then bite into the respective bone fragments to secure the tabs to the bone fragments. A bending tool (not shown) is utilized to bend the tabs 20, 21 and apply the compressive force against the bone fragments. For smaller fragments, the tabs may be manually bendable by the surgeon to press tabs against the bone fragments and cause the teeth of the tabs to bite into the fragments. In any event, the tabs 20, 21 have sufficient length to extend over the surfaces of the bone fragments and the tabs are suitably rigid to provide adequate strength to apply the transverse forces to the bone fragments. The tabs can have the same thickness as the plate.

The tabs can also be secured together by a pin 30, which extends in the distal and proximal fragments and across the fracture as shown in FIGS. 5 and 6. The pin 30 is installed in the tabs 20, 21 and the ends of the pins are then bent back against the tabs. The pin 30 provides a further degree of stabilization of the fracture.

The tabs 20, 21 can be initially in the plane of the plate, as shown in FIG. 13, and bent outwardly of the plate either manually or by the bending tool to extend adjacent to the surfaces of the bone fragments.

The tabs may be provided with holes 27 to receive the bending tool and enable the bending of the tabs.

The tabs may be provided with stress relief holes or notches 32 to direct the line of bending of the tabs in a particular direction.

The tabs can apply the compressive force to the fragments directly. Alternatively and, particularly for larger plates, after the tabs have been bent to face the bone fragments, screws or pins 28 can be used to develop the compressive force against the bone such as by providing the holes 27 with threads and thread ably advancing the screw or pins 33 in the holes. The screws or pins 33 can also provide an additional means to secure the tabs to the fragments by advancing into the bone.

FIG. 9 is an explanatory view showing the forces F1, F2 applied by the tabs 20, 21 against the bone fragments.

The forces F1 and F2 are transverse to the bone and have components which apply compressive force across the oblique fracture 13. Because forces F1 and F2 are longitudinally spaced by a distance d along the longitudinal axis of the bone, they produce a force couple or torque T opposing displacement of the bone fragments (sliding along the fracture line) which would produce bone shortening. The tabs 20, 21 also provide a counter-rotational torque to oppose rotation of the fracture site which would produce shortening of the bone. After the tabs 20, 21 have been bent against the bone fragments and before bone screws 17 or 19 have been inserted, the fixation plate can be rotated clockwise or counter clockwise respectively to increase or decrease the compressive pressure of the tabs against the bone fragments to adjust the compression of the bone fragments across the fracture.

Although two tabs 20, 21 have been shown in the drawings, it is also possible to employ only one tab (20 or 21) to achieve the compression across the fracture and the counter-resisting torque. Thus, for example, if only tab 20 is provided, it can apply force F1. The attachment of plate 15 by screws 17 to the distal fragment will provide opposed resistance corresponding to force F2 to achieve the compression across the fracture and the counter-resistant torque when force F1 is applied by tab 20. Preferably, however, tabs 20, 21 are provided on opposite sides of the plate as this permits greater control of the applied transverse forces. Additionally, more than one tab can be provided on the opposite sides of the plate to distribute the transverse forces over a greater length.

Figure 10:
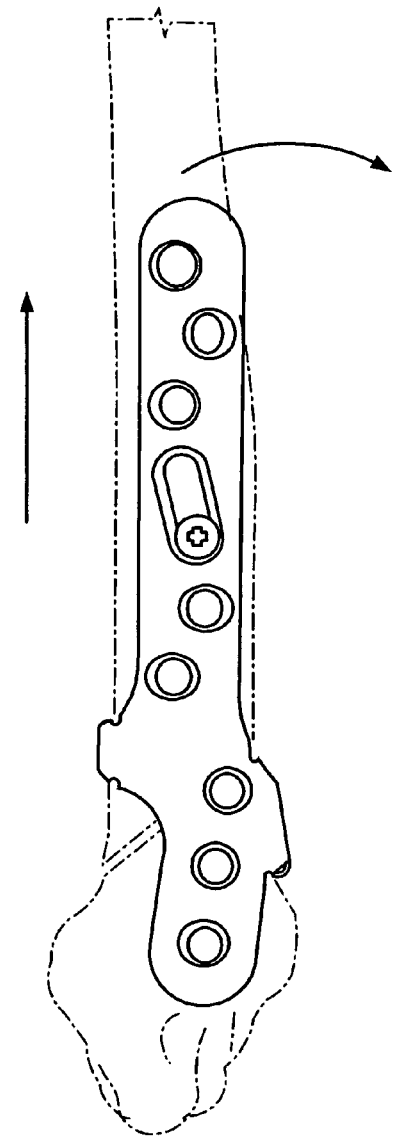
FIG. 10 is a view similar to FIG. 6 showing a modification of the fixation plate.

To facilitate the adjustment of the compression across the fracture, one of the holes in the proximal portion 18 for receiving a bone screw 19 is formed as an oblong hole 28 tilted upwardly in FIG. 10 in the direction from the distal portion 16 to the proximal position 18. Thus, if the proximal fragment is displaced in a direction away from the distal fragment, the fixation plate 15 will be urged to rotate clockwise, pressing the tab 20 against the proximal fragment and the tab 21 against the distal fragment with increasing force to increase the compression across the fracture. Movement in the opposite direction will relieve the compression. The oblong hole 28 also serves the function of fine tuning the installation of the plate. In this regard, the bone screw is loosely placed in the center of the oblong hole 28 to allow sliding of the plate along the screw which causes the plate to rotate and produce varied compression force applied by the tabs against the bone fragments.

The plate 15 is shaped to accommodate itself to the particular bone being treated, e.g. the lateral malleolus of the ankle. Thus, as seen in FIG. 6, the plate 15 is outwardly curved at its forward end adjacent to the distal fragment and then the plate follows the configuration of the bone as the plate extends rearwardly. In the transverse or cross-sectional direction, the plate is curved or bent outwardly as shown in FIG. 8 to extend over and around the lateral surface of the bone.

In a modification as shown in FIGS. 11-12, the forward end of the plate is extended and is provided with a downwardly bent lip 29 for engaging the distal surface of the distal fragment 10 so that pressure can be applied by the lip to the distal fragment in a direction to apply compression force at the fracture site. The lower end of the lip can be provided with teeth to bite into the distal fragment to secure the lip to the fragment.

Although the invention has been described with reference to specific embodiments, it will be apparent to those skilled in the art that numerous modifications and variations can be made within the scope and spirit of the invention as defined in the attached claims.

What is claimed is:

1. Apparatus for fixation of distal and proximal fragments of an oblique fracture in a bone, said apparatus comprising:
a fixation plate having a longitudinal axis adapted to extend along a long axis of a fractured bone and including a first portion extending along the longitudinal axis of the plate adapted for attachment to the distal fragment and a second portion extending in opposite direction from said first portion along the longitudinal axis of the plate adapted for attachment to the proximal fragment such that the plate is adapted to extend across the oblique fracture,
first and second elongate tabs extending transversely from the fixation plate for engaging the bone to apply force to the distal and proximal fragments in a direction adapted to extend transversely of the bone to produce a torque across the fracture, said first and second tabs extending outwardly from said first and second portions in opposite directions and being bendable in a direction away from a plane of the plate, said tabs being respectively connected to said first and second portions and having central longitudinal axes that intersect the longitudinal axis of the fixation plate at respective locations that are spaced longitudinally from one another along the longitudinal axis of the plate, said first and second tabs being provided with sufficient stiffness to apply said transverse forces to the bone fragments after being bent, to produce said torque to oppose destabilizing sliding of the fragments and produce the compressive force on the bone fragments, and fasteners to secure the first and second portions of the plate to the bone fragments, wherein said tabs extend predominantly perpendicular to said longitudinal axis of the late and intersect the late at respective locations that are offset longitudinally along the longitudinal axis of the plate.

2. Apparatus as claimed in claim 1, wherein said tabs are positioned for engaging respective upper and lower surfaces of the fragments, above and below the fracture on opposite sides of the fracture.

3. Apparatus as claimed in claim 2, wherein each of said tabs is provided with a bend line for directing bending of the tab at a specific location for enabling and facilitating bending of the tab around the bend line to permit an end portion of the tab to face and conformingly engage around a surface of the respective bone fragment.

4. Apparatus as claimed in claim 3, in which the bend lines are in the form a notch at the edge of the tab.

5. Apparatus as claimed in claim 2, wherein said tabs include projections having teeth to bite into the respective fragments.

6. Apparatus as claimed in claim 5, wherein said teeth are located at outer ends of the projections.

7. Apparatus as claimed in claim 5, wherein each of said tabs has a hole to facilitate bending the tabs with a bending tool.

8. Apparatus as claimed in claim 7, wherein said holes in the tabs are threaded.

9. Apparatus as claimed in claim 1, wherein the fixation plate is provided with holes for fasteners in the form of bone screws, said holes being located in said first and second portions.

10. Apparatus as claimed in claim 9, wherein at least one of said holes is oblong to allow sliding of the fixation plate along the bone before the bone screw in the oblong hole is tightened.

11. Apparatus as claimed in claim 10, wherein said oblong hole is oblique with respect to said longitudinal axis of the plate so that when the plate is longitudinally displaced, the plate will undergo rotation and change the pressure of the tabs against the fragments.

12. Apparatus as claimed in claim 1, wherein the fixation plate extends in a longitudinal direction and is curved in the longitudinal direction to conform with the bone.

13. Apparatus as claimed in claim 1, wherein in a transverse direction the plate is shaped to conform with the bone.

14. Apparatus as claimed in claim 13, wherein the fixation plate is shaped to conform to the lateral malleolus of an ankle.

15. Apparatus as claimed in claim 1, wherein the plate includes a tip at a forward end of the first portion to engage a distal surface of the distal fragment.

16. Apparatus as claimed in claim 1, comprising a pin connecting said tabs together.

17. A fixation plate for fixation of oblique fractures of the lateral malleolus of the ankle bone, said fixation plate comprising an elongated body having a first portion for attachment to a distal fragment of the oblique fracture of the lateral malleolus and a second portion for attachment to a proximal fragment of the oblique fracture of the lateral malleolus, the plate having a longitudinal axis and being of a length adapted for extending across the oblique fracture in opposite directions along the longitudinal axis of the plate and predominantly along the longitudinal axis of the fractured bone, and first and second tabs extending transversely in opposite directions from the first and second portions, said tabs having central longitudinal axes that intersect the longitudinal axis of the fixation plate at respective locations that are spaced longitudinally from one another along said longitudinal axis of the plate, the first tab being disposed at a lower edge of one of said portions for engaging an outer surface of one of the bone fragments and the second tab being disposed at an upper edge of the other of said portions for engaging an outer surface of the other of said bone fragments, said tabs being located on said plate for being positioned on opposite sides of the oblique fracture and above and below the oblique fracture and being bendable for contact with the bone on upper and lower surfaces thereof to produce forces in opposite directions on the fragments spaced longitudinally from one another to develop a counter resistant torque to oppose displacement of the fragments causing shortening of the bone, wherein said tabs extend predominantly perpendicular to said longitudinal axis of the plate and intersect the slate at respective locations that are offset longitudinally along the longitudinal axis of the plate.

18. The fixation plate as claimed in claim 17, wherein said tabs have outer ends with pointed teeth for biting into the respective fragments.

19. The fixation plate as claimed in claim 17, wherein the tabs have holes to facilitate bending thereof.

20. The fixation plate as claimed in claim 17, wherein the plate is shaped longitudinally and transversely to conform to the lateral malleolus.

21. Apparatus as claimed in claim 1, wherein said first and second tabs extend predominantly parallel to one another.

22. Apparatus as claimed in claim 17 wherein the first and second portions are connected together to form said plate as a predominantly rectangular body from which said first and second tabs extend outwardly.

23. Apparatus as claimed in claim 1, wherein the tabs extend from respective locations along an elongate portion of the fixation plate, said locations being spaced from one another along the longitudinal axis of the fixation plate.

24. Apparatus as claimed in claim 17, wherein the tabs extend from respective locations along an elongate portion of the fixation plate, said locations being spaced from one another along the longitudinal axis of the fixation plate.

25. A method for use of the apparatus of claim 1 to fix an oblique fracture comprising the steps of:
   (a) reducing the fracture by abutting proximal and distal fragments along the oblique fracture;
   (b) applying the fixation plate of the apparatus along the fractured bone and across the fracture such that the first portion of the fixation plate is adjacent to the distal fragment and the second portion of the fixation plate is adjacent to the proximal fragment;
   (c) disposing the tabs at positions at which one tab faces an upper surface of the bone while another tab faces a lower surface of the bone; and
   (d) bringing the tabs into contact with the upper and lower surfaces of the bone to apply force to the distal and proximal fragments of the bone to produce a torque that opposes destabilizing sliding of the fragments.

* * * * *